United States Patent [19]

Haffey et al.

[11] Patent Number: 5,087,445
[45] Date of Patent: Feb. 11, 1992

[54] PHOTOPROTECTION COMPOSITIONS HAVING REDUCED DERMAL IRRITATION

[75] Inventors: Janet G. Haffey, Norwalk; Jay R. Garfinkel, Wallingford, both of Conn.; Roy L. Blank, Spring Valley, N.Y.

[73] Assignee: Richardson-Vicks, Inc., Shelton, Conn.

[21] Appl. No.: 404,751

[22] Filed: Sep. 8, 1989

[51] Int. Cl.$^5$ .................. A61K 7/40; A61K 7/42; A61K 7/44; A61K 9/10

[52] U.S. Cl. .................................... 424/59; 424/60; 514/938

[58] Field of Search .................... 424/60, 59

[56] References Cited

U.S. PATENT DOCUMENTS 4,937,370  6/1990  Intaldli et al. ................... 560/45
4,999,186  3/1991  Sabatelli et al. ................ 424/60

Primary Examiner—Dale R. Ore
Attorney, Agent, or Firm—David K. Dabbiere; Anthony D. Sabatelli; Douglas C. Mohl

[57] ABSTRACT

The present invention relates to sunscreen compositions for substantially daily use containing effective sunscreening agents for both UVA and UVB radiation which are not readily absorbed by the skin; which have increased sunscreen protection and decreased chance for allergy, irritation, or toxicity problems resulting from daily or almost daily use; and which are less susceptible to rub off. These sunscreen compositions provide a constant and even protection against both UVA and UVB radiation and which are cosmetically acceptable. Furthermore, the present invention relates to methods for protecting the skin of humans or lower animals from the effects of UVA and UVB wavelength radiation. This method comprises topically applying to the skin on a substantially daily basis an effective coating of a sunscreen composition of the present invention.

10 Claims, No Drawings

PHOTOPROTECTION COMPOSITIONS HAVING REDUCED DERMAL IRRITATION

TECHNICAL FIELD

This invention relates to photoprotection compositions, substantially for daily use, having reduced dermal irritation. These compositions are useful for protecting the skin from the harmful effects of ultraviolet radiation, such as sunburn and sun-induced premature aging of the skin.

BACKGROUND OF THE INVENTION

The damaging effects of sunlight on skin are well documented. Contrary to what most people believe, it is not necessary that one sunbathe to suffer the ill-effects of excessive UV exposure. In fact, a lot of damage can be done just by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e. sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard or erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed., Chapter 26, pp. 499-511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15-24 (1982); and U.S. Pat. No. 4,387,089, DePolo, issued June 7, 1983; the disclosures of all of which are incorporated herein by reference. Hence, although the immediate effects of ultraviolet radiation may be cosmetically and socially gratifying, the long-term hazards are cumulative and potentially serious.

The fact that these effects are taken seriously by the general public is suggested by considering the sun protection products' market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

Sunblock agents are commercially available to protect the skin from UV radiation. These agents scatter or reflect ultraviolet radiation. Examples include titanium dioxide and zinc oxide. However, compositions containing these agents are opaque, generally unattractive in color, and are viewed as unacceptable for usage on more than just the nose or tops of the ears. Furthermore, these agents are very susceptible to rub-off or wear-off resulting in little or no protection.

The most common agents for sun protection are sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. To be most effective, sunscreens must be on the skin as a continuous uniform film. Delivering such a film to the surface of the skin is very difficult; maintaining the film over time is almost impossible. Sunscreens must remain on the surface of the skin during exposure. However, sunscreens are easily rubbed off or washed off by sweating or swimming and can also be lost to penetration into the skin. Sunscreening agents often cause irritation to the skin and eyes, primarily burning or stinging, respectively. This response can be more pronounced with daily or almost daily use.

There remains a continuing need to identify new compositions that have reduced dermal irritation when used on a daily basis which are effective for protecting the skin from ultraviolet radiation in both the UVA and UVB radiation ranges. It is accordingly an object of the present invention to provide sunscreen compositions containing effective sunscreening agents for both UVA and UVB radiation which are not readily absorbed by the skin; which have increased sunscreen protection and decreased chance for allergy, irritation, or toxicity problems resulting from daily or almost daily use; and which are less susceptible to rub off. A still further object is to provide sunscreen compositions which provide a constant and even protection against both UVA and UVB radiation and which are cosmetically acceptable.

It is an object of the present invention to provide a topical composition in a stable form, the use of which will prevent both acute (erythema) and chronic (photoaging) effects of exposure to the sun.

It is further an object of the present invention to provide a photoprotection composition having reduced dermal irritation especially when used on a daily or almost daily basis.

It is a still further object of the present ivention to provide a photoprotection composition which can be applied to the skin in advance of UV exposure without significant loss of efficacy.

These and other objects will become readily apparent from the detailed description which follows.

SUMMARY OF THE INVENTION

The present invention relates to sunscreen compositions having reduced dermal irritation when used on a daily or almost daily basis. These compositions are effective for absorbing ultraviolet radiation in both the UVA and UVB wavelength range. These sunscreen compositions comprise: (1) sunscreen agents which are compounds which have both a selected UVA-absorbing chromophore moiety and a selected UVB-absorbing chromophore moiety covalently linked together in the same molecule; and (2) specific copolymers of a carboxylic acid monomer and one or more higher alkylate esters.

By substantially daily use is meant that the compositions of the present invention can be applied on a daily, almost daily basis, or continued basis as opposed to occasional or recreational use as is the case with beach-type sunscreen products.

DETAILED DESCRIPTION OF THE INVENTION

Sunscreen Agents

The sunscreen agents useful in the present invention are those whose molecules have two distinct chromophore moieties which exhibit different ultraviolet radiation absorption spectrums. In particular, one of the chromophore moieties absorbs predominantly in the UVB radiation range, and the other absorbs strongly in the UVA radiation range. These molecules have the chromophore moieties linked in the molecule by covalent bonding. This covalent linkage can be such that the two chromophore moieties are directly coupled, i.e., their electrons are shared. Alternatively, this covalent linkage can be such that the two chromophore moieties do not have their electron systems directly coupled with each other.

More particularly, one of the chromophore moieties is characterized as being effective for strongly absorbing radiation in the UVA range when that chromophore moiety is isolated in an independent molecule. The other chromophore moiety is characterized as being effective for absorbing radiation predominantly within the UVB range when that chromophore moiety is isolated in an independent molecule. Finally, the linking moiety which covalently incorporates these two types of chromophore moieties into a single molecule is one which does not allow the electron systems of the two chromophore moieties to be coupled directly with each other. Thus, the sunscreen agents useful in the present invention are compounds having the general structure:

X-G-Z.

In this general structure, the X group is a UVA-absorbing chromophore that is a substituted, carbonyl-containing, aromatic ring-containing moiety. This UVA-absorbing moiety when isolated as an independent chromophore would exhibit at least one absorption maximum (designated herein as λmax, and described more fully hereinafter) within the wavelength range of from about 320 to about 400 nm. This absorption maximum would exhibit a molar absorptivity value (designated herein as "ε", and calculated as described hereinafter) of at least about 9,000, preferably at least about 20,000, and most preferably at least about 30,000.

The Z group in the above general structure is a UVB-absorbing chromophore that is a substituted, carbonyl-containing, aromatic ring-containing moiety. This UVB-absorbing moiety, when isolated as an independent chromophore, would exhibit a molar absorptivity value, ε, of at least about 4,000, preferably at least about 15,000, and most preferably at least about 25,000, for at least one wavelength within the range of from about 290 to about 320 nm. Preferably, when present as the sole chromophore in a molecule as hereinafter defined, the Z group exhibits at least one absorption maximum λmax within the range of from about 290 to about 320 nm. This absorption maximum preferably has a molar absorptivity value ε of at least about 4,000, more preferably at least about 15,000, and most preferably at least about 25,000. Finally, when present as the sole chromophore in a molecule as hereinafter defined, the Z group furthermore should not exhibit a λmax having a ε greater than about 9,000 for any wavelength above about 320 nm.

The third component of the above general structure, i.e., the G group, covalently bonds the X and Z chromophore moieties, but which separates the electron systems of the two chromophore moieties such that the two chromophore moieties do not have their electron systems directly coupled with each other. For example, the G linking moiety may be a straight or branched chain alkyl group having from about 1 to about 6 carbon atoms, a straight or branched chain alkyloxy group having from about 1 to about 6 carbon atoms, or straight or branched alkylamino group having from about 1 to about 6 carbon atoms.

Alternatively, G is a chemical bond or linking moiety which covalently bonds the two X and Z chromophore moieties such that the electron systems of these chromophores are directly coupled, i.e., electrons are shared. Preferred is G selected from a single bond, or atoms or groups of atoms which have free electrons which may be shared with both chromophore moieties, such as —O— and —NR— (wherein R is H, straight or branched chain alkyl having from about 1 to about 20 carbon atoms, $(CH_2CH_2O)_m$—H, or $(CH_2CH(CH_3)O)_m$—H, wherein m is an integer from 1 to about 8, and preferably m=1 to about 3). Most preferred is G being —NH— and, especially, —O—.

These sunscreen agents are fully disclosed in U.S. Pat. No. 4,999,186 to Sabatelli et al., issued Mar. 12, 1991, and U.S. Pat. No. 4,937,370 to Sabatelli, issued June 26, 1990, which are both incorporated herein by reference.

The sunscreen agents of the present invention preferably absorb light in the visible wavelength range (i.e., above about 400 nm) only weakly or not at all. The compounds are therefore either only lightly colored (e.g., light yellow or cream colored) or are essentially white. This is desirable for cosmetic reasons. Thus, the sunscreen agents preferably do not have a ε of greater than about 500 for any wavelength above about 400 nm, and most preferably the ε is essentially zero for any wavelength above about 400 nm.

It is further preferred that the compounds of the present invention be lower molecular weight compounds, preferably having a molecular weight of less than about 2,500, and most preferably less than about 1,000. Furthermore, the compounds are preferably liquids above about 10°.

Specifically, examples of suitable X chromophore moieties useful in the sunscreen compounds of the present invention include:

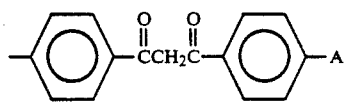

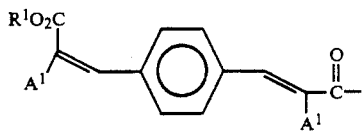

-continued

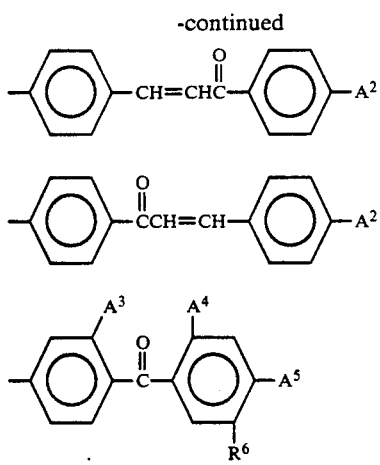

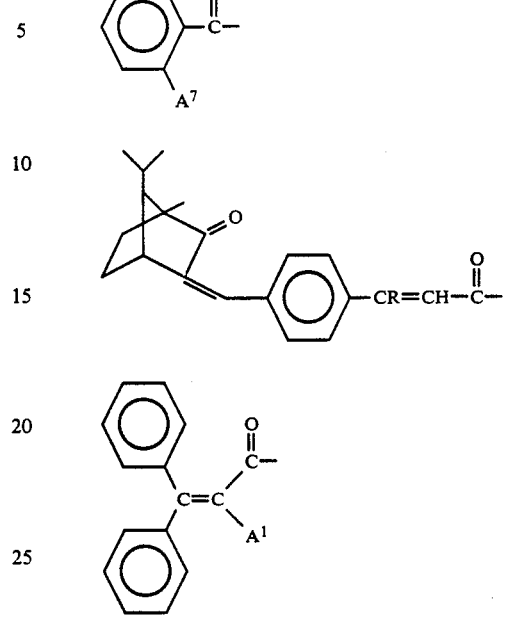

In all the preceding formulae, each A is a substituent independently selected from the group consisting of R, —OR, —NR@, or —SO$_3$H, or its pharmaceutically-acceptable salt or ester; each A$^1$ is independently —CN or —CO$_2$R$^1$; each A$^2$ is independently —OR or —NR$_2$; each A$^3$ is independently H or OH; each A$^4$ and A$^5$ are, independently, R or OR, and wherein further either A$^3$ or A must be OH; each A$^6$ is independently H or —SO$_3$H, or its pharmaceutically-acceptable salt or ester; each R is independently H, straight or branched chain alkyl having from about 1 to about 20 carbon atoms, (CH$_2$CH$_2$O)p—H, or (CH$_2$CH(CH$_3$)p—H, wherein p is an integer from 1 to about 8, and preferably p=1 to about 3; and each R$^1$ is independently straight or branched chain alkyl having from about 1 to about 20 carbon atoms.

Preferred as the X chromophore moiety are the groups

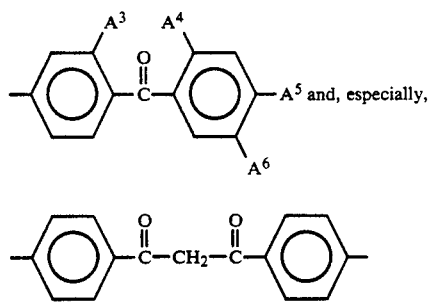

Preferably, either A$^3$ or A$^4$ is OH, with the other group being H; A$^5$ is R; and A$^6$ is H. Most preferably, A$^3$ is OH, and A$^4$, A$^5$ and A$^6$ are H. A is preferably R, and most preferably A is H.

Also, specific examples of the Z chromophore moieties useful in the sunscreen compounds of the present invention include:

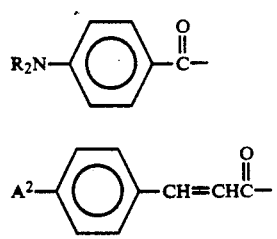

In these preceding formulae, each A$^7$ is independently —OR or —O$_2$C—R$^1$, exept that both A$^7$ and A$^3$ (described hereinbefore for the X groups) are not —OH; and the A$^1$, A$^2$, R and R$^1$ substituent groups are as described hereinbefore for the substituted X groups.

Preferred as the Z chromophore moiety are the groups

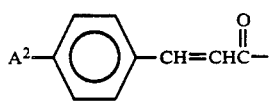

and, especially,

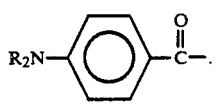

Preferably, —NR$_2$ is —NR$^1$$_2$. Both R$^1$ groups may be different alkyl groups. Particularly preferred is one R$^1$ group having more than about 2 carbon atoms (especially branched-chain alkyl groups, e.g., 2-ethyl-hexyl), the other R$^1$ group being methyl or ethyl, especially methyl. Alternatively preferred, both R$^1$ groups are the same alkyl group, preferably 2-ethyl-hexyl. Also preferred is A$^2$ being —OR or —NR$_2$ (preferably the —NR$_2$ is —NR$^1$$_2$ as described hereinbefore). Most preferred A$^2$ is —OCH$_3$, —OCH$_2$CH$_3$, OH, or —NR$^1$$_2$ (wherein one R$^1$ group has more than about 2 carbon atoms, especially branched-chain alkyl, and the other R$^1$ group is methyl or ethyl, especially methyl).

The Y linking moieties useful in the compounds of the present invention include the generically described moiety:

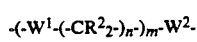

wherein each $W^1$ and $W^2$ is, independently, selected from the group consisting of a single bond, or, preferably, a moiety selected from the group of O or NR (wherein R is as described hereinbefore); n is an integer of 1 or greater, preferably n equals an integer from 1 to about 6; m is integer of 1 or greater, preferably m is 1 or 2; and each $R^2$ group is independently selected from the group consisting of H, OH, or straight or branched chain alkyl having from 1 to about 20 carbon atoms, preferably $R^2$ is H, OH, methyl or ethyl.

Useful G linking moiety groups include:

—O—(—$CH_2$—)$_n$—O—, wherein n is an integer from 1 to about 6;

—NH—(—$CH_2$—)$_n$—NH—, wherein n is an integer from 1 to about 6;

—(—O—$CH_2CH_2$—)$_n$—O—, wherein n is 1 or 2;

—(—NH—$CH_2CH_2$—)$_n$—NH—, wherein n is 1 or 2;

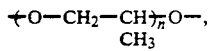

wherein n is 1 or 2;

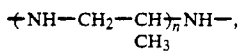

wherein n is 1 or 2; and

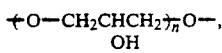

wherein n is 1 or 2.

A particularly preferred G group is —$OCH_2CH_2O$—.

Preferred sunscreening agents are 4-N,N-(2-ethylhexy)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)-dibenzoylmethane; N-N-di-(2-ethylhexyl)-4-aminobenzoic acid ester of 2-hydroxy-4-(2-hydroxyethoxy)benzophenone, and N,N-di(2-ethylhexyl)4-aminobenzoic acid ester of 4-(2-hydroxyethoxy)-dibenzoylmethane and mixtures thereof.

The sunscreen agents of the present invention can be prepared from commercially-available, chromophore-containing molecules. Typically, the synthesis of the sunscreen agents will be achieved by an esterification or amidation reaction. Synthesis techniques which are generally applicable for synthesizing sunscreen agents of the present invention are taught, for example, in U.S. Pat. No. 4,002,733, issued Jan. 11, 1977, to Degen et al.; and in U.S. Pat. No. 4,115,547, issued Sept. 19, 1978, to Degen et al.; the disclosures of both these patents being incorporated herein by reference. Representative procedures for synthesizing the sunscreen agents of the present invention are provided in the Examples hereinafter.

The term "pharmaceutically-acceptable salts and esters", as used herein, means those ester or salt forms of the sunscreen agents which are acceptable from a toxicity viewpoint. Pharmaceutically-acceptable salts include alkali metal (e.g., sodium and potassium), alkaline earth metal (e.g., calcium and magnesium), non-toxic heavy metal (e.g., stannous and indium), and ammonium and low molecular weight substituted ammonium (e.g., mono-, di-, tri- and tetra-substituted amine which are substituted with methyl and/or ethyl) salts. Preferred are the sodium, potassium, and ammonium salts. Pharmaceutically acceptable esters include straight or branched chain alkyl ester having from 1 to about 20 carbon atoms, preferably the methyl or ethyl ester.

The term "independent chromophore", as used herein, means the chromophore moiety (i.e., either the X or Z group) when it is bonded to —O—$R^3$ (wherein $R^3$ represents a short chain alkyl group, e.g., methyl or ethyl; preferably methyl) rather than the chromophore moiety being bonded to the Y linking moiety within the X-Y-Z compound. For example, independent chromophores of Compound 5 described hereinbefore are the ethyl ester of 4-N,N-butylmethylaminobenzoic acid and 2-hydroxy-4-methoxy-benzophenone. Also as an example, independent chromophores of Compound 8 described hereinbefore are the methyl ester of 4-N,N-(2-ethylhexyl)methylaminobenzoic acid and 4-methoxydibenzoylmethane.

The term "molar absorptivity value", as used herein, is a quantitative measure of the ability of a molecule to absorb ultraviolet light at a specified wavelength. The molar absorptivity value is expressed at a particular wavelength of light as the molar absorption coefficient (represented herein by " " which is expressed in units of liter/mole cm), which is calculated by the equation:

$$\epsilon = \frac{A}{lc}$$

wherein "l" is the path length (in centimeters) of the absorbing media through which the light passes; "c" is the concentration of the chromophore molecule (in moles per liter); and "A" is the "absorbance". The absorbance is calculated from the observed difference in the intensity of the particular wavelength of light before and after passing through the chromophore-molecule-containing absorbing media. Thus, the absorbance is calculated by the equation:

$$A = \log_{10} \frac{I_0}{I}$$

wherein "$I_0$" is the intensity of a particular wavelength of incident radiation on an absorbing path; and "I" is the intensity of the same particular wavelength of transmitted radiation which has passed through the absorbing path.

The calculation of the molar absorptivity value for a particular wavelength of light is well-known in the art, and is taught in more detail in *Atlas of Spectral Data and Physical Constants for Organic Compounds*, 2nd Ed., Vol. I, pp. 399-408 (Grasselli and Ritchey, Editors; CRC Press, Inc., Cleveland, Ohio, 1975), the disclosures of which are incorporated herein by reference. Instruments useful for making the intensity measurements for the calculation of the molar absorptivity value are also well-known in the art (eg., Varion DMS-100 and Beckman DU-7). Molar absorptivity values for representative compounds of the present invention are provided in the Examples hereinafter.

The term "absorption maximum", as used herein, means a wavelength of radiation at which the chromophore-containing molecule has the greatest molar absorptivity value relative to wavelengths immediately above and below the absorption maximum wavelength. Thus, in the typical spectrum of UV-radiation absorption, an absorption maximum is easily identified as a peak in the graph of the spectrum generated by the instrument measuring the UV absorption. Absorption maximum (designated herein as max) are provided for representative sunscreen compounds of the present invention in the Examples hereinafter.

The sunscreen agents useful in the present invention have several desirable properties relative to a simple mixture of a UVA-absorbing molecule with a UVB-absorbing molecule. One benefit is the certainty of providing both UVA and UVB protection at the same site on the skin. A mixture of molecules may lack this uniformity due to non-uniform distribution onto the skin surface and/or selective penetration by one type of molecule through the skin versus the other type of molecule. A related benefit is that the sunscreen agents of the present invention provide a constant relative proportion of UVA to UVB protection because one chromophore cannot be more readily lost from the skin (e.g., by a higher rate of rub-off or skin penetration) than the other chromophore. Another benefit is that the sunscreen agents of the present invention are absorbed more slowly by the skin than mixtures of the independent chromophores. This translates into longer duration of protection for the skin, and less potential for skin irritation resulting form absorption by the skin. Furthermore, the sunscreen agents useful in the present invention provide this long-lasting, constant UV radiation protection at least as effectively as a freshly-applied mixture of independent chromophores, and in some instances the protection is stronger and more broad-spectrum than the mixture. (The ability of the compounds of the present invention, and of mixtures of independent chromophores, to absorb UV radiation may be measured by in vitro methods known generally in the art, such as those taught in Sayre et al., "A Comparison of in vivo and in vitro Testing of Sunscreening Formulas", Photochem. Photobiol., 29, 559–566 (1979), the disclosures of which are incorporated herein by reference.) Some of the compounds of the present invention may also be more resistant to wash-off by water from sweat or swimming.

The sunscreen agents of the present invention typically comprise from about 0.1% to about 20.0% by weight of the sunscreen compositions of the present invention, preferably from about 1% to about 20%, and most preferably from about 5% to about 15%.

Carboxylic Copolymer

The carboxylic copolymers useful in the present invention are polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula

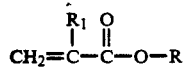

wherein R is an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of crosslinking monomer is from about 0.2 to 0.4 weight percent. The preferred crosslinking monomers are allyl pentaerythritol, trimethylolpropane diallylether or allyl sucrose. These polymers are fully described in U.S. Pat. No. 4,509,949, Huang et al., issued Apr. 5, 1985.

The carboxylic monomers useful in the production of polymers used in this invention are the olefinically-unsaturated carboxylic acids containing at least one activated carbon-to-carbon olefinic double bond, and at least one carboxyl group.

The preferred carboxylic monomers are the acrylic acids having the general structure

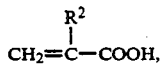

wherein $R^2$ is a substituent selected from the class consisting of hydrogen, halogen, and the cyanogen (-C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The polymers are crosslinked with a polyfunctional vinylidene monomer containing at least 2 terminal $CH_2<$ groups, including for example, butadiene, isoprene, divinyl benzene, divinyl naphthlene, allyl acrylates, and the like. Particularly useful crosslinking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. Most preferred is Carbomer 1342 (available as Carbopol 1342 from B. F. Goodrich).

These polymers comprise from about 0.025 to about 0.75, preferably from about 0.05 to about 0.25 and most preferably from about 0.075 to about 0.175.

Pharmaceutically-acceptable Sunscreen Carriers:

In addition to a sunscreen agent as described hereinbefore, the sunscreen compositions of the present invention essentially contain a pharmaceutically-acceptable sunscreen carrier. The term "pharmaceutically-acceptable sunscreen carrier", as used herein, means one or more substantially non-irritating compatible filler diluents which are suitable for topical application to the skin of a human or lower animal. The term "compatible", as used herein, means that the components of the carrier must be capable of being comingled with the sunscreen agent, and with each other, in a manner such that there is no interaction which would substantially reduce the efficacy of the composition during use for protecting the skin from the effects of UVA and UVB wavelength radiation. Pharmaceutically-acceptable sunscreen carriers must, of course, be of sufficiently high purity and sufficiently low toxicity to render them suitable for topical administration to the human or lower animal.

The sunscreen compositions of the present invention contain pharmaceutically-acceptable sunscreen carriers selected as appropriate for the formulation desired. For example, it is possible to prepare sunscreen compositions of the present invention in the form of organic solvent solutions, aqueous emulsions, gels, or aerosol formulation. Preferred are sunscreen compositions of the present invention formulated as aqueous emulsions. The pharmaceutically-acceptable sunscreen carriers useful in the compositions of the present invention include, for example, water, oils, fats, waxes, synthetic polymers, emulsifiers, surfactants, perfumes, dyes, preservatives, artificial tanning agents (e.g., dihydroxyacetone), and conventional sunscreening agents (e.g., octyl N,N-dimethyl-paraaminobenzoate; 2-hydroxy-4-methoxybenzophenone).

Water is typically the major component of the sunscreen compositions of the present invention. Generally, water is present at a level of from about 50% to about 99% by weight of the composition, preferably from about 60% to about 90%, and most preferably from about 65% to about 75%.

Emulsifiers are preferably included in the sunscreen compositions of the present invention, preferably comprising from about 0.5% to about 10% by weight of the composition, and most preferably from about 0.5% to about 4%. Preferred emulsifiers are anionic or nonionic although other types may also be used. Most preferred is anionic. Suitable emulsifiers are disclosed in, for example, U.S. Pat. No. 3,755,560, issued Aug. 28, 1973, to Dickert et al.; U.S. Pat. No. 4,421,769, issued Dec. 20, 1983, to Dixon et al.; and McCutcheon's *Detergents and Emulsifiers*, North American Edition, 1983; with the disclosures of these references being incorporated herein by reference.

Types of emulsifiers useful in the sunscreen compositions of the present invention include ethoxylated fatty acids, ethoxylated esters, ethoxylated ethers, ethoxylated alcohols, phosphated esters, polyoxyethylene fatty ether phosphates, fatty acid amides, acyl lactylates, soaps and mixtures thereof. Fatty alcohols such as cetyl and stearyl alcohol, and cetearyl alcohol are also regarded as emulsifiers for purposes of the present invention.

Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium steroyl-2-lactylate and calcium stearoyl-2-lactylate. Soaps are also acceptable emulsifiers. The soaps may be formulated in situ in processing the compositions and are preferably alkali metal or triethanolamine salts of long-chain fatty acids. Such soaps include sodium stearate, triethanolamine stearate and the similar salts of lanolin fatty acids.

Also preferred for use in the compositions of the present invention is a copolymer of ethylene and acrylic acid. These monomers:

Ethylene: $CH_2=CH_2$

Acrylic Acid: 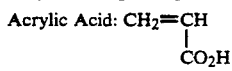

are present in polymeric form as follows:

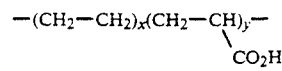

wherein the ratio of x:y is from about 1:24 to about 1:9. The weight average molecular weight is from about 3,500 to about 4,500, preferably from about 4,000 to about 4,300.

The compositions of the present invention may also contain in addition to the aforementioned components, a wide variety of additional oil soluble materials and/or water soluble materials.

Among the oil soluble materials are non-volatile silicone fluids such as dimethicones, cyclomethicones and polydimethyl siloxanes with viscosities ranging from about 10 to about 100,000 centistokes at 25° C. These siloxanes are available from Dow Corning Corporation as the Dow Corning 200 series. Cyclomethicones are available in the 300 series.

Other oil soluble materials include fatty acid alcohols such as cetyl alcohol and stearyl alcohol; esters such as cetearyl palmitate, lauryl myristate and isopropyl palmitate; oils such as castor oil, jojoba oil, cottonseed oil, peanut oil and sesame oil; waxes such as petrolatum, ceresin wax, carnauba wax, beeswax, and castor wax; cetyl palmitate and glyceryl tribehenate; lanolin, its derivatives and components such as acetylated lanolin, lanolin alcohols and lanolin fatty acids; oil soluble powders such as aluminum starch octenyl succinate. Sterols such as soyasterol, cholesterol and phytosterol are also useful herein. Highly preferred for use herein are isodecyl neopentanoate, isohexadecane and $C_{12}$-$C_{15}$ alcohols benzoate (available as Finsolv TN from Finetex).

These optional oil phase materials may individually comprise up to about 20% by weight of the total sunscreen composition, preferably from about 10% to about 15%.

Additional water soluble materials may also be present in the compositions of this invention. Included are humectants such as glycerine, hexylene glycol, sorbitol, propylene glycol, alkoxylated glucose and hexanetriol; tyrosine; thickening agents such as carboxyvinyl polymers (Carbopols ®—offered by B. F. Goodrich Company, such polymers are described in detail in U.S. Pat. No. 2,798,053, issued July 2, 1957 to Brown, incorporated herein by reference); ethyl cellulose, polyvinyl alcohol, carboxymethyl cellulose, vegetable gums and clays such as Veegum ® (magnesium aluminum silicate, R. T. Vanderbilt, Inc.); proteins and polypeptides; preservatives such as the methyl, ethyl, propyl and butyl esters of hydroxybenzoic acid (Parabens—Mallinckrodt Chemical Corp.), EDTA, methylisothiazolinone and imidazolidinyl ureas (Germall 115—Sutton Laboratories); and pH controlling agents such as sodium hydroxide, potassium hydroxide or citric acid, if desired. Additional materials include UV scattering powders (e.g., titanium dioxide) and antioxidants such as propylene glycol (and) BHA (and) propyl gallate (and) citric acid, as well as chelators such as disodium EDTA.

The water phase materials may individually comprise up to about 25% by weight of the total sunscreen composition, preferably up to about 15%.

The present compositions may also contain agents suitable for aesthetic purposes such as perfumes and/or dyes.

The pH of the sunscreen compositions herein is preferably in the range of from about 4.5 to about 9.

For an aqueous emulsion sunscreen composition of the present invention, the mean particle size of the dispersed oil phase materials (e.g., sunscreen agent, polymer, perfumes, etc.) dispersed in the aqueous phase may be in the range of from about 5 to about 10 microns with greater than about 75% of the particles being less than about 12 microns.

The pharmaceutically-acceptable sunscreen carriers, in total, typically comprise from about 0.1% to about 99.8% by weight of the sunscreen compositions of the present invention, preferably from about 80% to about 99%, and most preferably from about 85% to about 95%.

The compositions of the present invention may be prepared using the method described in the examples hereinafter.

Method for Preventing Sunburn

The present invention further relates to a method for protecting the skin of humans or lower animals from the effects of UVA and UVB wavelength radiation, such as sunburn and premature aging of the skin. Such a method comprises topically applying to the human or lower animal an effective coating of a sunscreen agent of the present invention, or, preferably, of a sunscreen composition of the present invention. The term "effective coating", as used herein, means a film of sunscreen agent sufficient to substantially reduce the amount of UVA and UVB wavelength light which reaches the skin's surface. Typically, an effective coating of the skin is from about 0.5 mg sunscreen agent of the present invention/cm² skin to about 5 mg sunscreen agent of the present invention/cm² skin.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

A sunscreen composition is prepared by combining the following components as described below.

| Components | % w/w |
| --- | --- |
| Water, purified | q.s. to 100% |
| 4-N-decylaminobenzoic acid 4-ester of 2-hydroxy-4-(2-hydroxyethoxy)benzophenone | 9.00 |
| Isodecyl Neopentanoate (available as Dermol 105 from Bernel Chemical) | 8.00 |
| Carbomer 1342 (available as Carbopol 1342 from B. F. Goodrich) | 0.10 |
| Triethanolamine (TEA) | 0.10 |
| Steareth-21 (available as Brig. 721 from ICI Americas) | 1.00 |
| Steareth-2 (available as Brig. 72 from ICI Americas) | 0.75 |
| Glycerin | 1.00 |
| Imidazolidinyl urea (available as Germall 115 from Sutton Labs) | 0.10 |
| Methylparaben | 0.40 |
| Ethylparaben | 0.15 |
| Propylparaben | 0.20 |
| Cetyl alcohol | 1.00 |
| Stearyl Alcohol | 0.75 |

Combine Carbomer 1342, glycerin, methylparaben and imidazolidinyl urea with water while mixing and heat to 75° C. The triethanolamine is combined to this mixture and the resulting mixture is heated to 85° C. In a separate container, combine the remaining ingredients and heat to 85° C. with mixing to form the oil phase. The oil phase is then added to the water phase with mixing (high shear using, for example, a Lightnin mixer) at 85° C. The resulting composition is then cooled to room temperature.

This emulsion is useful for topical application to inhibit damage caused by acute or chronic UV exposure. Use of an amount of this composition sufficient to deposit about 2.0 mg/cm² of the sunscreening agent to the skin on a substantially daily basis prior to UV exposure is appropriate and will result in little or no dermal irritation.

EXAMPLE 2

A sunscreen composition is prepared as described above in Example 1.

| Components | % w/w |
| --- | --- |
| Water, purified | q.s. to 100% |
| 4-N,N-(2-ethylhexyl)methylaminobenzoic acid of 2-hydroxyethoxy)benzophenone | 9.00 |
| Steareth-21 | 1.00 |
| Steareth-2 | 0.75 |
| Methylparaben | 0.40 |
| Imidazolidinyl urea | 0.10 |
| Ethylparaben | 0.15 |
| Propylparaben | 0.20 |
| Isodecyl Neopentanoate | 8.00 |
| Glycerin | 1.00 |
| Cetyl alcohol | 1.00 |
| Stearyl Alcohol | 0.75 |
| TEA | 0.20 |
| Carbomer 1342 | 0.20 |

This emulsion is useful for topical application to inhibit damage caused by acute or chronic UV exposure. Use of an amount of this composition sufficient to deposit about 2.0 mg/cm² of the sunscreening agent to the skin on a substantially daily basis prior to UV exposure is appropriate and will result in little or no dermal irritation.

EXAMPLE 3

A sunscreen composition is prepared as described above in Example 1.

| Components | % w/w |
| --- | --- |
| Water, purified | q.s. to 100% |
| 4-N,N-(2-ethylhexyl)methylaminobenzoic acid of 2-hydroxyethoxy)benzophenone | 9.00 |
| Carbomer 1342 | 0.30 |
| Methyl Paraben | 0.30 |
| Hexylene Glycol | 1.00 |
| DEA Cetyl Phosphate (available as Amphisol from Bernel Chemical) | 1.00 |
| Ethylparaben | 0.15 |
| Cetyl alcohol | 1.00 |
| Stearyl Alcohol | 0.50 |
| TEA | 0.30 |
| Benzyl Alcohol | 0.30 |

This emulsion is useful for topical application to inhibit damage caused by acute or chronic UV exposure. Use of an amount of this composition sufficient to deposit about 2.0 mg/cm² of the sunscreening agent to the skin on a substantially daily basis prior to UV exposure is appropriate and will result in little or no dermal irritation.

EXAMPLE 4

A sunscreen composition is prepared as described above in Example 1.

| Components | % w/w |
| --- | --- |
| Water, purified | q.s. to 100% |
| Carbomer 1342 | 0.10 |
| Methyl Paraben | 0.30 |
| Hexylene Glycol | 1.00 |
| 4-N-decylaminobenzoic acid 4-ester of 2-hydroxy-4-(2-hydroxyethoxy)benzophenone | 9.00 |
| DEA Cetyl Phosphate | 1.00 |
| Ethylparaben | 0.15 |
| Cetyl Alcohol | 1.00 |
| Stearyl Alcohol | 0.50 |
| TEA | 0.10 |
| Benzyl Alcohol | 0.30 |

This emulsion is useful for topical application to inhibit damage caused by acute or chronic UV exposure. Use of an amount of this composition sufficient to deposit about 2.0 mg/cm$^2$ of the sunscreening agent to the skin on a substantially daily basis prior to UV exposure is appropriate and will result in little or no dermal irritation.

EXAMPLE 5

A sunscreen composition is prepared as described above in Example 1.

| Components | % w/w |
| --- | --- |
| Water, purified | q.s. to 100% |
| Carbomer 1342 | 0.50 |
| Methylparaben | 0.30 |
| Hexylene Glycol | 1.00 |
| 4-N,N-(2-ethylhexyl)methylaminobenzoic acid 4-ester of 2-hydroxy-4-(2-hydroxyethoxy)benzophenone | 6.00 |
| 4-N,N-(2-ethylhexyl)methylaminobenzoic acid ester of 4-(2-hydroxyethoxy)dibenzoylmethane | 3.00 |
| DEA Cetyl Phosphate | 1.00 |
| Ethylparaben | 0.15 |
| Cetyl Alcohol | 1.00 |
| Stearyl Alcohol | 0.50 |
| TEA | 0.10 |
| Benzyl Alcohol | 0.30 |

This emulsion is useful for topical application to inhibit damage caused by acute or chronic UV exposure. Use of an amount of this composition sufficient to deposit about 2.0 mg/cm$^2$ of the sunscreening agent to the skin on a substantially daily basis prior to UV exposure is appropriate and will result in little or no dermal irritation.

EXAMPLE 6

A sunscreen composition is prepared as described above in Example 1.

| Components | % w/w |
| --- | --- |
| Water, purified | q.s. to 100% |
| Carbomer 1342 | 0.10 |
| Methyl Paraben | 0.30 |
| Hexylene Glycol | 1.00 |
| 4-N,N-(2-ethylhexyl)methylaminobenzoic acid 4-ester of 2-hydroxy-4-(2-hydroxyethoxy)benzophenone | 6.00 |
| 4-N,N-(2-ethylhexyl)methylaminobenzoic acid ester of 4-(2-hydroxyethoxy)dibenzoylmethane | 3.00 |
| DEA Cetyl Phosphate | 1.00 |
| Ethylparaben | 0.15 |
| Cetyl Alcohol | 1.00 |
| Stearic Acid | 0.50 |
| TEA | 0.10 |
| Benzyl Alcohol | 0.30 |
| Isodecyl Neopanoate | 10.00 |
| Isohexadecane | 3.00 |
| C$_{12}$-C$_{15}$ alcohols benzoate | 4.00 |
| Glycerin | 1.00 |
| Aluminum starch Octenyl succinate | 1.00 |
| Glyceryl tribehenate | 3.00 |
| Antioxidant | 0.10 |
| Disodium EDTA | 0.10 |

This emulsion is useful for topical application to inhibit damage caused by acute or chronic UV exposure. Use of an amount of this composition sufficient to deposit about 2.0 mg/cm$^2$ of the sunscreening agent to the skin on a substantially daily basis prior to UV exposure is appropriate and will result in little or no dermal irritation.

EXAMPLE 7

A sunscreen composition is prepared as described above in Example 1.

| Components | % w/w |
| --- | --- |
| Water, purified | q.s. to 100% |
| 4-N,N-(2-ethylhexyl)methylaminobenzoic acid ester of 4-(2-hydroxyethoxy)dibenzoylmethane | 9.00 |
| Isodecyl Neopentanoate | 8.00 |
| Carbomerl 1342 | 0.10 |
| TEA | 0.10 |
| Methylparaben | 0.30 |
| Hexylene Glycol | 1.00 |
| Ethylparaben | 0.15 |
| Benzyl Alcohol | 0.30 |
| Cetyl Alcohol | 1.00 |
| Stearyl Alcohol | 0.75 |
| DEA Cetyl Phosphate | 1.00 |

This emulsion is useful for topical application to inhibit damage caused by acute or chronic UV exposure. Use of an amount of this composition sufficient to deposit about 2.0 mg/cm$^2$ of the sunscreening agent to the skin on a substantially daily basis prior to UV exposure is appropriate and will result in little or no dermal irritation.

What is claimed is:

1. A sunscreen composition substantially for daily use comprising:

(A) from about 0.1% to about 20.0% of a sunscreen compound selected from the group consisting of 4-N,N-dimethylaminobenzoic acid 4-ester of 2-hydroxy-4-(2-hydroxyethoxy)benzophenone; 4-methoxycinnamic acid 4-ester of 2-hydroxy-4-(2-hydroxyethoxy)-benzophenone; 4-(2-methylpropoxy)cinnamic acid 4-ester of 2-hydroxy-4-(2-hydroxyethoxy)benzophenone; 4-N-decylaminobenzoic acid 4-ester of 2-hydroxy-4-(2-hydroxyethoxy)benzophenone; 4-N,N-butylmethylaminobenzoic acid 4-ester of 2-hydroxy-4-(2-hydroxyethoxy)benzophenone; 4-N,N-(2-ethylhexyl)methylaminobenzoic acid 4-ester of 2-hydroxy-4-(2-hydroxyethoxy)benzophenone; 4-N,N-butylmethylaminobenzoic acid ester of 4-(2-hydroxyethoxy)dibenzoylmethane; 4-N,N-(2- ethylhexyl)methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxy-ethoxy)benzophenone; and N,N-di-(2-ethylhexyl)-4-aminobenzoic acid ester of 4-(2-hydroxyethoxy)dibenzoylmethane;

(B) from about 0.025% to about 0.75% of a carboxylic copolymer comprising polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula

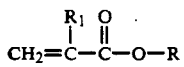

wherein R is an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups; and (C) from about 0.1% to about 99.8% of a pharmaceutically-acceptable sunscreen carrier.

2. A sunscreen composition according to claim 1, wherein the acrylate ester of the carboxylic copolymer is stearyl methacrylate, and wherein the copolymer comprises from about 0.2 to 0.4 weight percent of the crosslinking monomer selected from the group consisting of allyl pentaerythritol, trimethylolpropane diallylether and allyl sucrose.

3. A sunscreen composition according to claim 2 which further comprises from about 0.5% to about 10% of an emulsifier.

4. A sunscreen composition according to claim 3 which further comprises from about 1% to about 15% of an oil soluble material.

5. A sunscreen composition according to claim 4 wherein said oil soluble material is selected from the group consisting of isodecyl neopentanoate, isohexadecane and $C_{12}$-$C_{15}$ alcohols benzoate and mixtures thereof.

6. A method for protecting the skin of humans or lower animals from the effects of UVA and UVB wavelength radiation, said method comprising topically applying to the skin of the human or lower animal on a substantially daily basis an effective coating of a sunscreen composition according to claim 1.

7. A method for protecting the skin of humans or lower animals from the effects of UVA and UVB wavelength radiation, said method comprising topically applying to the skin of the human or lower animal on a substantially daily basis an effective coating of a sunscreen composition according to claim 2.

8. A method for protecting the skin of humans or lower animals from the effects of UVA and UVB wavelength radiation, said method comprising topically applying to the skin of the human or lower animal on a substantially daily basis an effective coating of a sunscreen composition according to claim 3.

9. A method for protecting the skin of humans or lower animals from the effects of UVA and UVB wavelength radiation, said method comprising topically applying to the skin of the human or lower animal on a substantially daily basis an effective coating of a sunscreen composition according to claim 4.

10. A method for protecting the skin of humans or lower animals from the effects of UVA and UVB wavelength radiation, said method comprising topically applying to the skin of the human or lower animal on a substantially daily basis an effective coating of a sunscreen composition according to claim 5.

* * * * *